United States Patent [19]
Kroll

[11] Patent Number: 6,093,982
[45] Date of Patent: Jul. 25, 2000

[54] HIGH VOLTAGE OUTPUT ARRAY SWITCHING SYSTEM

[76] Inventor: Mark W. Kroll, 651 Carnellon Ct., Simi Valley, Calif. 93065

[21] Appl. No.: 08/749,440

[22] Filed: Nov. 15, 1996

[51] Int. Cl.⁷ .............................. H01H 19/14; A61N 1/18
[52] U.S. Cl. .......................... 307/115; 307/113; 307/125; 607/5
[58] Field of Search .................................. 607/2, 5, 7, 8, 607/63; 307/108, 109, 110, 112, 113, 115, 116, 125, 71

[56] References Cited

U.S. PATENT DOCUMENTS

| | | | |
|---|---|---|---|
| 4,900,947 | 2/1990 | Weiner et al. | 307/110 |
| 5,369,351 | 11/1994 | Adams | 320/121 |
| 5,383,907 | 1/1995 | Kroll | 607/5 |
| 5,405,363 | 4/1995 | Kroll et al. | 607/5 |
| 5,407,444 | 4/1995 | Kroll | 607/5 |
| 5,444,310 | 8/1995 | Kataoka et al. | 307/125 |
| 5,484,452 | 1/1996 | Persson | 607/5 |
| 5,635,776 | 6/1997 | Imi | 307/110 |

*Primary Examiner*—Jeffrey Gaffin
*Assistant Examiner*—Jonathan S. Kaplan
*Attorney, Agent, or Firm*—Brad Pedersen

[57] ABSTRACT

A high voltage array switching system utilizes an array of low voltage charge storage devices to generate a relatively high energy, high voltage output required by battery powered devices such as implantable cardioverter defibrillators. The system includes a low voltage battery system having a supply voltage connection and a ground connection. N low voltage charge storage devices are provided, with each charge storage device having one of an anode and a cathode electrically connected to the supply voltage and having the other of the anode and the cathode electrically connected to the ground connection. M configuration switches are electrically connected between the charge storage devices and the battery system. A control system selectively controls the configuration switches to charge the charge storage devices in a configuration in which at least some of the charge storage devices are in parallel and discharge the charge storage devices in a configuration in which at least some of the charge storage devices are switched to be in series. In the system, the number N of low voltage charge storage devices is greater than four and is also greater than or equal to M, the number of configuration switches.

13 Claims, 1 Drawing Sheet

HIGH VOLTAGE OUTPUT ARRAY SWITCHING SYSTEM

FIELD OF THE INVENTION

The present invention relates to battery powered devices requiring high energy, high voltage outputs, such as implantable cardioverter defibrillators. More particularly, the present invention relates to a high voltage output array switching system for utilizing an array of low voltage charge storage devices to generate a high voltage output.

BACKGROUND OF THE INVENTION

Implantable cardioverter defibrillator (ICD) systems are good examples of a battery powered device which requires a relatively high energy, high voltage output. ICD systems attempt to treat cardiac arrhythmias by passing through the heart muscle a cardioversion or defibrillation countershock, depending on the type of cardiac arrhythmia diagnosed. The objective of the cardioversion or defibrillation countershock is to immerse as much of the myocardium as possible within the electrical field generated by the countershock. The countershock is a truncated capacitive discharge of electrical energy that generally ranges from 50 to 750 volts and from 0.1 to 40 joules.

One of the problems common to all ICD systems is generation of the necessary high voltage, large energy countershock from a low voltage battery supply within the device. Almost all current ICD systems which have been approved by the Food and Drug Administration (FDA) utilize a flyback transformer to increase the low voltage of a lithium silver vanadium oxide (SVO) battery to a much higher voltage which is then stored in a high voltage output capacitor to be discharged as the electrical countershock. Examples of this kind of high voltage output circuitry are shown in U.S. Pat. Nos. 4,774,950 and 5,405,363.

While the SVO battery works well in generating the necessary current to power the flyback transformer so as to develop a high voltage charge in a relatively short amount of time, e.g., less than 10–20 seconds, the SVO cells are relatively inefficient power storage devices in terms of their energy density. As a result, it is difficult to decrease the size of an ICD system which utilizes an SVO battery arrangement.

One alternative arrangement which addresses this problem has been described in U.S. Pat. Nos. 5,383,907 and 5,407,444. In this system an intermediate high current output power storage device, such as a rechargeable battery, is used to power the flyback transformer, with the intermediate power storage device being powered from a low current output battery that is more efficient in terms of energy density than traditional SVO cells.

A different approach is described in U.S. Pat. No. 5,369,351 in which the flyback transformer and high voltage charge storage capacitors are eliminated in favor of a high voltage charge storage array comprised of a large bank of switchable, rechargeable low voltage battery cells. While this system has the advantage of eliminating two of the larger components within an ICD system, the technique requires a large number of electronic switches to allow for the batteries to be charged in parallel at a low voltage and then switched into series to be discharged at a high voltage. In this system, at least two electronic switches are required for each rechargeable battery cell. As a result, the construction and control of such a high voltage charge storage array is more complicated than for a traditional flyback transformer and output capacitor system.

Although there are several different existing systems for developing high voltage outputs in ICD systems, it would be desirable to provide an alternative high voltage output system for an ICD system which can result in further reduction of the size of the ICD system and also simplify the design and control of the high voltage output system.

SUMMARY OF THE INVENTION

The present invention is a high voltage array switching system which utilizes an array of low voltage charge storage devices to generate a relatively high energy, high voltage output required by battery powered devices such as implantable cardioverter defibrillators. The system includes a low voltage battery system having a supply voltage connection and a ground connection. N low voltage charge storage devices are provided, with each charge storage device having one of an anode and a cathode electrically connected to the supply voltage and having the other of the anode and the cathode electrically connected to the ground connection. M configuration switches are electrically connected between the charge storage devices and the battery system. A control system selectively controls the configuration switches to charge the charge storage devices in a configuration in which at least some of the charge storage devices are in parallel and discharge the charge storage devices in a configuration in which at least some of the charge storage devices are switched to be in series. In the system, the number N of low voltage charge storage devices is greater than four and is also greater than or equal to M, the number of configuration switches.

The present invention improves over U.S. Pat. No. 5,369,351 by decreasing the complexity required to charge the low voltage storage devices in parallel and then discharge them in series to provide the high voltage output required for effective defibrillation. In a preferred embodiment, the present invention utilizes double layer, low voltage electrochemical capacitors known as super capacitors as the low voltage charge storage device. In an alternate embodiment, the low voltage charge storage device can be a rechargeable battery.

BRIEF DESCRIPTION OF THE DRAWINGS

FIG. I is a schematic diagram of one embodiment of the present invention.

DETAILED DESCRIPTION OF THE PREFERRED EMBODIMENT

Figure 1:
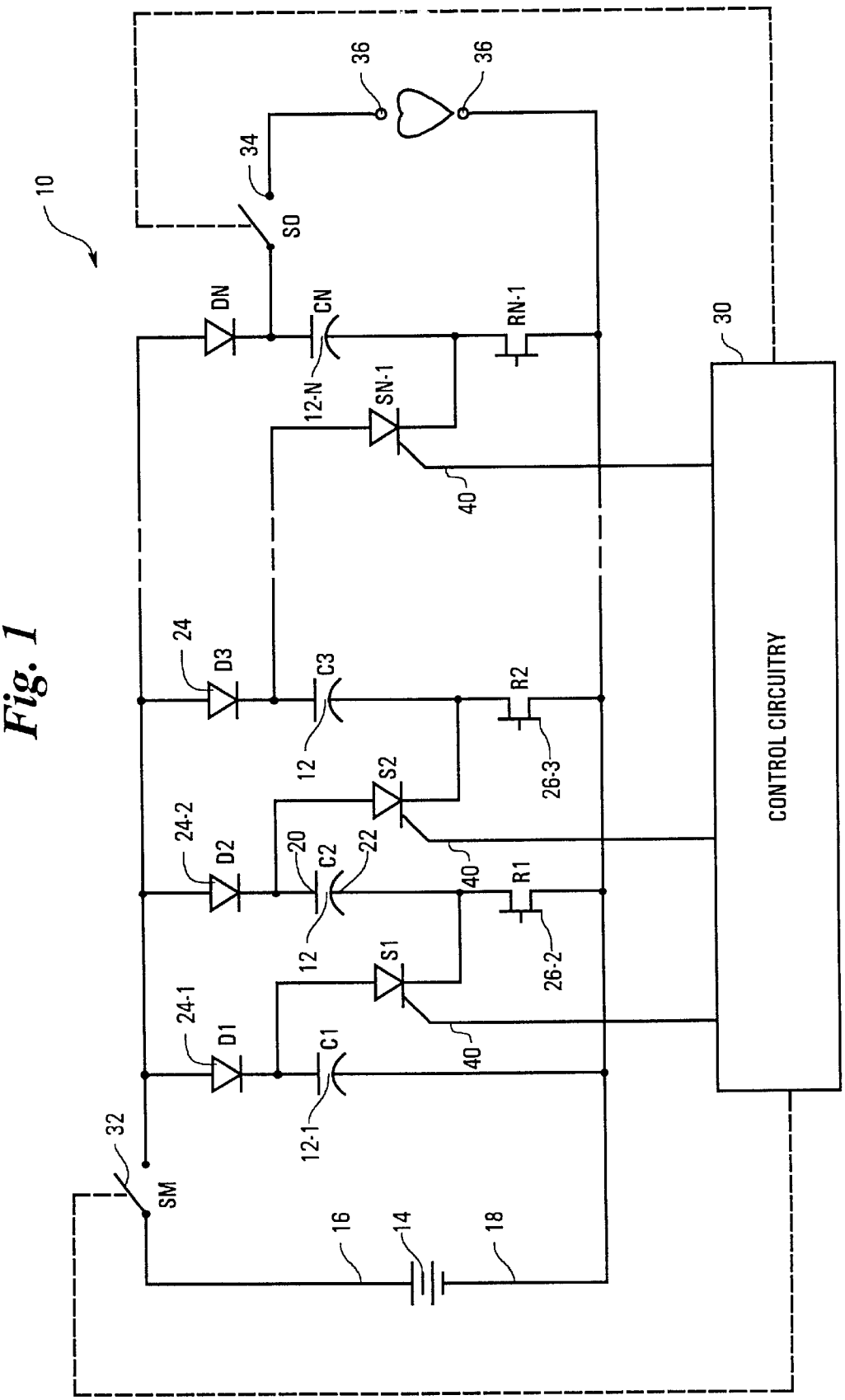

Referring now to FIG. 1, the preferred embodiment of the present invention will now be described. A high voltage array switching system 10 in accordance with the present invention utilizes an array of low voltage charge storage devices 12 to generate a relatively high energy, high voltage output from a low voltage battery system 14. Examples of battery powered devices requiring these type of relatively high energy, high voltage outputs include implantable cardioverter defibrillator (ICD) systems, implantable drug pumps, implantable high voltage nerve or tissue stimulating devices and the like.

The low voltage battery system 14 has a supply voltage connection 16 and a ground connection 18. The choice of the battery chemistry and charging capabilities of low voltage battery system 14 will depend upon the output requirements of the particular device. For an ICD system, for example, it may be necessary to recharge the low voltage charge storage devices in a relatively short time (less than 20–30 seconds) in order to deliver a second defibrillation countershock in the event that a first countershock is unsuccessful. In the embodiment shown in FIG. 1, low voltage battery system 14 is a high current battery, such as a lithium silver vanadium oxide (SVO) battery. In the embodiment shown in FIG. 2, low voltage battery system 14 is a lower current, higher energy density battery, such as a Lithium Iodine (LI) battery or a Lithium Carbon Monofluoride (LiCFx) battery.

As shown in FIG. 1, there are N low voltage charge storage devices 12. Each charge storage device 12 has one of an anode 20 and a cathode 22 electrically connected to the supply voltage 16 and having the other of the anode 20 and the cathode 22 electrically connected to the ground connection 18. Preferably, a diode 24 is connected to the anode 20 of each charge storage device to control the direction of charging. As with low voltage battery 14, the choice of charging/discharging characteristics of charge storage devices 12 will be dependent upon the particular application required by the device which uses array switching system 10. It will also be apparent that the particular voltage characteristics of the low voltage battery 14 and charge storage devices 12 can either be matched directly (i.e., both having similar output voltages), or a voltage doubler or the like can be used to increase the output voltage of the low voltage battery 14 to the charge storage devices 12. In FIG. 1, low voltage charge storage devices 12 are double layer, low voltage electrochemical capacitors, known as super capacitors. Low voltage charge storage devices could so be low voltage rechargeable batteries.

A control system 30 selectively controls the charging and discharging of the charge storage devices 12. Preferably, control system 30 is a programmable microprocessor or microcontroller as is well known in the art of ICD systems. Alternatively, the functions of control system 30 could be implemented in custom logic and circuit elements. In the embodiments shown in FIG. 1, control switch 32 is turned on by control system 30 to initiate a charge of charge storage devices 12. Typically, control system 30 would initiate a charge in response to some kind of sensed indication (i.e., a cardiac dysrhythmia). Alternatively, control system 30 could initiate a charge based on periodic timing or in response to an external control signal. Output switch 34 is used to control the discharge of the charge storage devices 12 through at least a pair of implantable electrodes 36, 38. It will be apparent to one skilled in the art that a variety of switch networks can be implemented for output switch 34 to alter the output characteristics of the discharge (e.g., an H-bridge network to create a bi-phasic waveform), and that electrodes 36, 38 can be a variety of electrodes (e.g, endocardial, epicardial, subcutaneous, nerve stimulating) depending upon the particular application of the implantable device.

M configuration switches 40 are electrically connected between the charge storage devices 12 and the battery system 14. Configuration switches 40 are each connected to control system 34 and are used to charge the charge storage devices in a configuration in which at least some of the charge storage devices 12 are in parallel and discharge the charge storage devices 12 in a configuration in which at least some of the charge storage devices 12 are switched to be in series. Preferably, configuration switches 40 are silicon controller rectifier switches (SCRs), although configuration switches could also be implemented as FET, bipolar transistor or IGBET switches or the like, depending upon the switching and output characteristics of the device.

In the array switching system 10, the number N of low voltage charge storage devices 12 is greater than four and is also greater than or equal to M, the number of configuration switches 40. This difference between the number N of low voltage charge storage device 12 and the number M of configuration switches 40 can be seen in that there is no configuration switch 40 connected to the cathode 22 of the first charge storage device 12-1; nor is there a configuration switch 40 connected to the anode 20 of the last charge storage device 12-n..

In operation, control system 30 closes control switch 32 to initiate a charge of charge storage devices 12. This charges charge storage device 12-1 through diode 24-1. Charge storage device 12-2 is charged through diode 24-2 and a return component 26-2. Preferably, return component 26 is connected between the cathode 22 and the ground connection 18 in all but one of the charge storage devices 12. All of rest of charge storage devices 12-3 through 12-n are charged in a similar manner to charge storage device 12-2.

Return component 26 is shown in FIG. 1 as a switched field-effect-transistor (FET) transistor, although return component 26 could also be a resistor, such as a 1 K ohm resistor,. Alternatively, return component 26 could also be implemented as a bipolar transistor, or an integrated bipolar transistor (IGBT). The advantage of using the resistor for return component 26 is that no switching is required, the advantage of using the FET transistor for return component 26 is that there is no resistive loss during delivery of the discharge output.

Control system 30 selectively controls the configuration switches 40 to charge the charge storage devices 12 in a configuration in which at least two of the charge storage devices 12 are configured in parallel. When the time comes to discharge the charge storage devices 12, control system 30 controls the configuration switches 40 to be set in a configuration in which at least two of the charge storage devices 12 are switched to be in series. In the case where all of the charge storage devices 12 are switched from parallel to series configuration, control system 30 simultaneously triggers configuration switches 40 to put all of the charge storage devices 12 in series with charge storage device 12-1 having cathode 22-2 connected to ground connection 18 and charge storage device 12-n having anode 20-n connected to output switch 34. In this way, output switch 34 sees the highest possible voltage available by the parallel combination of charge storage devices 12.

It will be apparent that numerous alternative configuration are possible in terms of output discharge from the present invention. For example, output switch 34 could be selectively connected to different charge storage devices 12 to produce a discharge in which some, but not all, of the charge storage devices are configured in parallel. Alternatively, the timing of control system 30 firing or shutting off configuration switches 40 could be altered to provide for a ramped (ascending or descending) discharge output. Still other discharge outputs such as sawtooth or curved waveforms are also possible.

What is claimed is:

1. A high voltage array switching system comprising:
   a low voltage battery system having a supply voltage connection and a ground connection;
   N low voltage charge storage devices, each charge storage device having one of an anode and a cathode electrically connected to the supply voltage and having the other of the anode and the cathode electrically connected to the ground connection;
   M configuration switches electrically connected between the charge storage devices and the battery system; and
   control means for selectively controlling the configuration switches to charge the charge storage devices in a configuration in which at least two of the charge storage devices are in parallel and discharge the charge storage devices in a configuration in which at least two of the charge storage devices are switched to be in series, wherein N and M are integers and N is greater than four and greater than or equal to M.

2. The high voltage array switching system of claim 1 wherein the charge storage devices are selected from the set consisting of: electrolytic capacitors, super capacitors and rechargeable electrochemical charge storage cells.

3. The high voltage array switching system of claim 1 wherein all but one of the charge storage devices includes a return component connected between the other of the anode and the cathode and the ground connection and wherein each configuration switch is uniquely electrically connected between the one of the anode and the cathode of a first low voltage charge storage device and the other of the anode and the cathode of another low voltage charge storage device.

4. The high voltage array switching system of claim 3 wherein the return component is selected from the set consisting of: a resistor, a bipolar transistor, an integrated bipolar transistor (IGBT) or a field-effect-transistor.

5. The high voltage array switching system of claim 1 wherein each of the low voltage charge storage device includes a diode connected between the one of the anode and the cathode of the capacitor and the supply voltage.

6. The high voltage array switching system of claim 1 wherein the control means includes:

a charging switch electrically connected between the battery system and the low voltage charge storage devices;

a high voltage output switching network electrically connected to the low voltage charge storage devices; and control logic electrically connected to the charging switch, the output switching network and the configuration switches.

7. The high voltage array switching system of claim 1 wherein array switching system is contained within a biocompatible housing as part of an implantable medical device.

8. A high voltage array switching system comprising:

a low voltage battery system having a supply voltage connection and a ground connection;

N low voltage charge storage devices, each charge storage device having one of an anode and a cathode electrically connected to the supply voltage and having the other of the anode and the cathode electrically connected to the ground connection;

M configuration switches electrically connected between the charge storage devices and the battery system;

a charging switch electrically connected between the battery system and the low voltage charge storage devices;

a high voltage output switching network electrically connected to the low voltage charge storage devices;

control system circuitry operably connected to the configuration switches, the charging switch and the output switching network so as to operate the configuration switches to charge the charge storage devices in a configuration in which at least two of the charge storage devices are in parallel when the charging switch is closed and the output switching network is open and discharge the charge storage devices in a configuration in which at least two of the charge storage devices are switched to be in series when the charging switch is open and the output switching network is closed, wherein N and M are integers and N is greater than four and greater than or equal to M.

9. The high voltage array switching system of claim 8 wherein the charge storage devices are selected from the set consisting of: electrolytic capacitors, super capacitors and rechargeable electrochemical charge storage cells.

10. The high voltage array switching system of claim 8 wherein all but one of the charge storage devices includes a return component connected between the other of the anode and the cathode and the ground connection and wherein each configuration switch is uniquely electrically connected between the one of the anode and the cathode of a first low voltage charge storage device and the other of the anode and the cathode of another low voltage charge storage device.

11. The high voltage array switching system of claim 10 wherein the return component is selected from the set consisting of: a resistor, a bipolar transistor, an integrated bipolar transistor (IGBT) or a field-effect-transistor.

12. The high voltage array switching system of claim 8 wherein each of the low voltage charge storage device includes a diode connected between the one of the anode and the cathode of the capacitor and the supply voltage.

13. The high voltage array switching system of claim 8 wherein array switching system is contained within a biocompatible housing as part of an implantable medical device.

* * * * *